United States Patent [19]

Weber et al.

[11] Patent Number: 4,709,094
[45] Date of Patent: Nov. 24, 1987

[54] SIGMA BRAIN RECEPTOR LIGANDS AND THEIR USE

[75] Inventors: Eckard Weber; Mark Sonders, both of Portland; John F. Keana, Eugene, all of Oreg.

[73] Assignee: State of Oregon, acting by and through the Oregon State Board of Higher Education, acting for and on behalf of the Oregon Health Sciences University and the University of Oregon, Portland, Oreg.

[21] Appl. No.: 884,150

[22] Filed: Jul. 10, 1986

[51] Int. Cl.$^4$ .......................................... C07C 129/12
[52] U.S. Cl. ...................................... 564/238; 514/634
[58] Field of Search .......................... 564/238; 514/634

[56] References Cited

U.S. PATENT DOCUMENTS

| 1,642,180 | 9/1927 | Scott | 564/238 |
| 1,672,431 | 6/1928 | Schotte | 564/238 |
| 1,915,922 | 6/1931 | Christmann | 564/238 |
| 2,633,474 | 3/1953 | Beaver | 564/238 |

FOREIGN PATENT DOCUMENTS

| 223410 | 10/1924 | United Kingdom | 564/238 |
| 258203 | 9/1926 | United Kingdom | 564/238 |
| 478525 | 1/1938 | United Kingdom | 564/238 |

Primary Examiner—Paul J. Killos
Attorney, Agent, or Firm—Millen & White

[57] ABSTRACT

1,3-Disubstituted-guanidines, e.g., of the formula

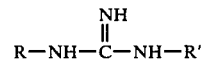

wherein R and R' are hydrocarbon groups which preferably are the same, e.g., 1,3-dibutyl-guanidine, 1,3-diphenyl-guanidine and 1,3-di-o-tolyl-guanidine, are highly selective ligands for sigma brain receptors and are useful in the diagnosis and treatment of hallucination associated psychotic mental illness and chronic mental depression. Tritium labeled 1,3-di-(o-tolyl)-guanidine is useful as a screening tool for compounds having selective sigma receptor binding activity, as it is displaced from isolated mammalian brain membrane to which it is bound portionately to the activity of such a compound.

23 Claims, No Drawings

SIGMA BRAIN RECEPTOR LIGANDS AND THEIR USE

BACKGROUND OF THE INVENTION

This invention relates to guanidine compounds which selectively bind sigma brain receptors, to pharmaceutical compositions comprising them, to methods for determining in vitro the sigma brain receptor binding activity of organic compounds and to the use of compounds having such activity in the diagnosis and treatment of mental illness.

A wide variety of substituted guanidines are disclosed in the patent literature. See. e.g., U.S. Pat. Nos. 1,411,231; 1,422,506; 1,597,233; 1,642,180; 1,672,431; 1,730,388; 1,795,738; 1,850,682; 2,145,214; 2,254,009; 2,274,476; 2,289,543; 2,633,474; 3,117,994; 3,140,231; 3,159,676; 3,228,975; 3,248,426; 3,252,861; 3,270,054; 3,283,003; 3,301,755; 3,320,229; 3,409,669; 3,547,951; 3,639,477; 3,784,643; 3,804,898; 3,968,243; 3,975,533; 4,007,181; 4,051,256; 4,060,640; 4,109,014; 4,161,541; 4,169,154; 4,393,077; 4,471,137.

U.S. Pat. No. 3,547,951 discloses 1,3-dioxolan-4-yl-alkyl-substituted guanidines which have anti-hypertensive activity. Disclosed as a possible substituent on the other amino group is lower alkyl, including n-butyl. U.S. Pat. No. 3,248,426, describes (Example 5) a 1,3-disubstituted guanidine whose substituents are hydrophobic hydrocarbon groups, one of which is napthylmethyl and the other is n-butyl. U.S. Pat. No. 3,975,533 discloses o-halo-benzylideneamino-guanidines and their use as anti-depressants for overcoming psychic depression. U.S. Pat. No. 4,169,154 discloses the use of guanidines in the treatment of depression. U.S. Pat. No. 3,639,477 discloses propoxyguanidine compounds as having anorectic properties.

Three compounds which we found to possess selective sigma receptor binding activity are 1,3-di-phenyl-guanidine, 1,3-di-o-tolylguanidine and 1,3-dibutylguanidine.

Certain benzomorphan opiates, such as N-allylnormetazocine (SKF 10,047) and cyclazocine, in addition to analgesia, cause hallucinations, depersonalization, drunkenness and other psychotomimetic effects in man. In monkeys, dogs and rodents the psychotomimetic opiates cause behavioral and autonomic effects that are unlike those observed with administration of classical opiates such as morphine or the opioid peptides. Specific sigma "opioid" receptors in the brain are believed to mediate such atypical effects. Martin et al, (1976) *J. Pharmacol. Exp. Ther.* 197, 517–532. The sigma receptors are believed to also mediate the psychotomimetic effects of phencyclidine [PCP, angel dust], or alternatively, that psychotomimetic opiates act at specifc PCP receptors. Zukin, R. S. & Zukin, S. R., (1981) *Mol. Pharmacol.* 20, 246–254; Shannon, H. E., (1983) *J. Pharmacol. Exp. Ther.* 225, 144–152; White, J. M. & Holtzman, S. G., (1983) *Psychopharmacology* 80, 1–9; and Zukin et al., (1986) *J. Neurochem.* 46, 1032–1041. PCP is a drug of abuse that causes a behavioral syndrome in man similar to that which is observed in schizophrenic psychosis. Aniline, 0. & Pitts, F. N. Jr., (1982) *CRC Critical Rev. Toxical.* 10, 145–177. Because of the potent psychotomimetic effects of sigma opiates and PCP, it is believed that sigma (or PCP) receptors play a role in mental illness, particularly schizophrenia.

A systematic investigation of the role of sigma receptors in normal and abnormal brain function has been hindered by a lack of specific sigma receptor binding assays and bioassays. Development of such specific assays requires well-characterized, highly selective and potent sigma receptor ligands. Recent studies have shown that brain membrane receptors can be labeled in vitro with $(\pm)[^3H]SKF$ 10,047, Su, T. P., (1982) *J. Pharmacol. Exp. Ther.* 223, 284–290; $(\pm)[^3H]$-Ethylketazocine, Tam, S. W., (1983) *Proc. Natl. Acad. Sci. U.S.A.* 80, 6703–6707; or with $(\pm)[^3H]SKF$ 10,047, Tam, S. W. & Cook, L. (1984) *Proc. Natl. Acad. Sci. U.S.A.* 81, 5618–56721; Martin, et al., (1984) *J. Pharmacol. Exp. Ther.* 231, 539–544; and Mickelson, M. M. & Lahti, R. A. (1985) *Res. Commun. Chem. Pathol. Pharmacol.* 47, 255,263 although not selectively, Gundlach et al., (1985) *Eur. J. Pharmacol.* 113, 465–466; and Largent B. L., Gundlach, A. L. & Snyder, S. H. (1986) *J. Pharmacol. Exp. Ther.*, (In Press), and with $(\pm)[^3H]$3-(3-hydroxyphenyl)N-(1-propyl)piperidine $((\pm)[^3H]$3-PPP), Largent et al., (1984) *Proc. Natl. Acad. Sci. U.S.A.* 81, 4983–4987, which is apparently more selective for sigma receptors than the others.

After the initial in vitro studies by Martin and collaborators (1976), Keats and Telford, Keats, A. S. and Telford, J., "Analgesics: Clinical Aspects" In: *Molecular Modification in Drug Design*, R. F. Gould, ed., Advances in Chemistry Series #45 Amer. Chem. Soc., Wash. D.C. (1964), and Haertzen, C. A. Cyclazocine and Nalorphine on the Addiction Research Center Inventory (ARCI), *Psychopharmacologia* (Berl.) 18, 366–377 (1970), numerous investigators set out to biochemically characterize the different opiate receptors (mu receptors, kappa receptors and sigma receptors) *in vitro*.

The first evidence for the existence of a separate sigma receptor in test tube experiments was provided by Su(1982) in a paper describing an etorphine-inaccesible binding site in guinea pig brain membranes which was apparently selectively labeled by tritium labeled SKF-10,047. To overcome the fact that SKF-10,047 could label multiple opioid receptors in the brain, Su performed his receptor binding assay using tritium labeled SKF-10,047 in the presence of excess unlabeled etorphine. Etorphine is a very strong opiate agonist drug which is known to bind to delta receptors, mu receptors and kappa receptors with almost equal potency. Su used etorphine to saturate all mu, kappa and delta receptors in a brain membrane preparation and then added tritium labeled SKF-10,047. This enabled him to detect a sigma binding site that was apparently different from mu, kappa and delta receptors.

A major breakthrough in identifying the sigma receptor as a separate entity occured when Tam et al., (1984) demonstrated that the previous problems in selectively labeling the sigma receptor were caused by the fact that in all previous experiments a racemic SKF-10,047 preparation was used. Tam showed that using a tritium labeled (+)-SKF-10,047 isomer he could selectively label a sigma receptor that was different from the mu, delta and kappa opioid receptors. On the other hand, Tam showed that (−)-SKF-10,047 apparently labeled the mu and kappa receptors but not the sigma receptors. Tam, S. W., *Eur. J. Pharm.* 109, 33–41 (1985). This finding has now been confirmed. (Martin et al, 1984). Moreover, there is evidence from behavorial experiments, Khazan et al., *Neuropharm.* 23, 983–987 (1984); Brady et al., *Science* 215, 178–180 (1981), that it is the (±)-SKF- 10,047 isomer that is solely responsible for the psychotomimetic effects of SKF-10,047.

One of the most important findings of the biochemical characterization of the sigma receptor has been that this receptor binds all synthetic opiate drugs that are known to have hallucinogenic and psychotomimetic effects. Opiates that do not have psychotomimetic effects in vivo do not bind to this receptor. Most importantly, it has been shown that besides hallucinogenic opiate drugs, the sigma receptor also binds many antipsychotic drugs that are used clinically to treat hallucinations in schizophrenic patients. (Tam and Cook, 1984). The initial observations with regards to antipsychotic drug binding to the sigma receptor (Su, 1982) were subsequently extensively confirmed and extended by Tam and Cook (1984), who also showed that when one used radioactively labeled haloperidol, one of the most potent antipsychotic drugs that is used clinically, about half of the binding sites in brain membrane preparations are actually sigma receptors whereas the other half of the binding sites are apparently dopamine receptors. It has long been known that all antipsychotic drugs are also dopamine receptor antagonists and previously the beneficial actions of antipsychotic drugs in psychotic patients have been attributed to the dopamine receptor blocking effect of these drugs. It is clear from the work by Tam, however, showing that antipsychotic drugs bind also to the sigma receptor and from the behavorial work described above, that the actions of antipsychotic drugs on the sigma receptor may in one way or another cause the beneficial effects of alleviating hallucinations. Taken together all these observations make the sigma receptor a prime candidate to be involved in the pathogenesis of mental illness, particularly schizophrenia in which hallucinations are a major clinical symptom.

The antipsychotic and anti-schizophrenic drugs that are currently in use have very strong side effects that are mainly due to their action on dopamine receptors. The side effects often involve irreversible damage to the extrapyramidal nervous system which controls movement functions of the brain. Patients under long term anti-schizophrenic drug treatment often develop a syndrome that involves permanent damage of their ability to control coordinated movement.

We have identified a novel class of compounds which bind to the sigma receptor.

The foregoing studies have shown that the sigma binding site has the characteristics of (1) stereoselectivity towards dextrorotatory benzomorphan opiates and insensitivity for naloxone; (2) high affinity for haloperidol and moderate to high affinity for phenothiazine antipsychotic drugs which are also known to be potent dopamine receptor blockers; and (3) insensitivity for dopamine and apomorphine. This intriguing drug selectivity profile calls for a thorough analysis of the role of sigma receptors in normal and abnormal brain function. In order to do so, it is essential that a spectrum of highly selective and potent sigma receptor active compounds be available. This invention provides such compounds and wants to identify other drugs having such activity.

OBJECTS OF THE INVENTION

It is an object of this invention to provide a novel class of compounds which selectively bind to sigma receptor sites.

It is another object to provide such a compound which is radioactively tagged and which is useful for assaying in vitro the sigma receptor binding activity of organic compounds.

It is a further object to provide pharmacological compositions comprising a compound having sigma receptor binding activity.

It is still another object to provide a method for determining the sigma receptor binding activity of organic compounds.

It is still another object to provide an in vitro screening method for assaying compounds having sigma receptor activity and utility as antipsychotic and antidepressant drugs.

It is still another object to provide a method of determining the relationship of abnormal psychotic-like behavior in a mammal displaying such behavior to sigma receptor system dysfunction.

Other objects will be apparent to those skilled in art to which this invention pertains.

SUMMARY OF THE INVENTION

In a composition aspect, this invention relates to the tritium labeled compound 1,3-di-(p-[$^3$H]-o-tolyl)-guanidine.

In another composition aspect, this invention relates to 1,3-di-(4-halo-2-methylphenyl)-guanidine.

In another composition aspect, this invention relates to a pharmaceutical composition, in unit dosage form and adapted for systemic administration to a human being, which comprises, per unit dosage, an amount effective to alter the sigma brain receptor-modulated activity of a human being displaying psychotic behavior or suffering from chronic depression, of a 1,3-disubstituted-guanidine in its water-soluble protonated form which displaces in vitro 1,3-di-(p-[$^3$H]-o-tolyl)-guanidine bound to isolated mammalian brain membrane.

In a method aspect, this invention relates to a method of determining the sigma brain receptor binding activity of an organic compound which comprises the steps of:

(a) contacting in an aqueous medium a known amount of isolated mammalian brain membrane which has psychotomimetic benzomorphan binding activity, with a mixture of (i) a tritium labeled 1,3-disubstituted guanidine which selectively binds sigma brain receptors, in a known amount capable of being bound to the sigma receptors of that brain membrane; and (ii) varying known amounts of a water soluble organic compound to be assayed for sigma receptor binding activity.

(b) separating the brain membrane from any of the tritium labeled compound which is not bound to the brain membrane in step (a);

(c) determining, from the molar relationship of the proportion of bound tritium labeled compound which is separated in step (b) to the molar amount of the organic compound employed in step (a), the sigma receptor binding activity of that organic compound.

In another method aspect, this invention relates to a method of determining the relationship of abnormal psychotic-like behavior in a mammal displaying such behavior to sigma receptor dysfunction, which comprises administering thereto a sigma brain receptor-modulating amount of water-soluble N,N' disubstituted-guanidine which displaces in vitro 1,3-di-(p-[$^3$H]-o-tolyl)-guanidine bound to mammalian brain membrane, effective to alter the sigma brain receptor-modulated mental activity of that mammal.

In another method aspect, this invention relates to a method of treating chronic depression or a psychotic mental illness associated with hallucinations which comprises administering thereto an amount of a water soluble N,N'- disubstituted-guanidine which displaces in vitro 1,3-di-(p-[³H]- o-tolyl)-guanidine bound to mammalian brain membrane, effective to ameliorate the depression or hallucinations, respectively.

DETAILED DISCUSSION

We have discovered that the disubstituted guanidines of this invention have sigma receptor binding activity, as evidenced by their ability to displace (±)-[³H]SKF 10,047 from guinea pig brain membrane binding sites. We have also found that an [³H]-labeled derivative of one of these compounds, viz., [³H]1,3-di-ortho-tolyl-guanidine (1,3-di-(p-[³H]-o-tolyl)-guanidine, ([³H]-DTG]), which has the formula:

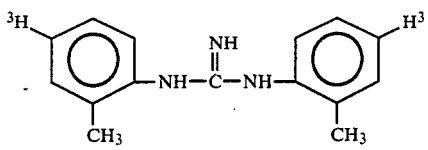

binds reversibly, saturably, selectively and with high affinity to sigma receptor binding sites in guinea pig brain membrane homogenates and slide-mounted rat and guinea pig brain sections. We have established that (±)-[³H]3-PPP binds to the same sites. Availability of the selective sigma ligands of this invention facilitates characterization of sigma receptors in vivo and in vitro.

The preferred N,N'-disubstituted guanidines of this invention are those of the formula

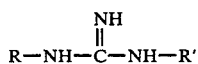

wherein R and R' each are an alkyl group of at least 4 carbon atoms or carbocyclic aryl groups of at least 6 carbon atoms, e.g., R and R', which are the same or different, are alkyl of 4 of more carbon atoms, e.g., a 4 to 12, preferably a straight chain and more preferably a 4 to 8 carbon atom alkyl group, for example, butyl, isobutyl, tert-butyl, amyl, hexyl, octyl, nonyl and decyl; cycloalkyl of 3 to 12 carbon atoms, e.g., cyclopropyl, cyclopentyl, cyclohexyl, cycloheptyl, 1,4-methylene-cyclohexane cyclopentylmethyl, cyclohexylmethyl, 1- or 2-cyclohexylethyl and 1-,2- or 3-clohexylpropyl; carbocyclic aryl, alkaryl or aralkyl, e.g., of up to 18 carbon atoms and containing 1-3 separate or fused aromatic rings, e.g., phenyl, benzyl, 1- and 2-phenyethyl, 1-, 2-, or 3-phenylpropyl; o-, m-, or p-tolyl, m,m'-dimethyl-phenyl, o-,m- or p,-ethylphenyl, m,m'-diethyl-phenyl, m-methyl-m'-ethylphenyl and o-propyl-phenyl, naphthyl, 2-naphthyl, and biphenyl.

Additionally, substituents which are chemically and physiologically substantially inert compared to the guanidine group may be present on the R and R' hydrocarbon groups, e.g., halo, such as chloro, bromo, iodo fluoro; nitro, trifluoromethyl, alkyoxy of 1-8 carbon atoms, e.g., methoxy, ethoxy and propoxy; acyloxy, e.g., alkanoyloxy of 1-8 carbon atoms, e.g., acetoxy and benzoxy, amido, e.g., acetamido, N-ethylacetamido, carbamide, e.g., carbamyl, N-methylcarbamyl, N,N'-dimethylcarbamyl, etc.

Especially preferred are compounds of formula I wherein R and R' each are substituted phenyl groups which preferably but not necessarily are identical, e.g., wherein the substituent is one or more of the foregoing substituents, for example, in the o-, m- or p-position or the o-, p- or m-,m'-position, when the phenyl group is disubstituted. Specific examples are those wherein R is o-tolyl and R' is p-bromo-o-tolyl, R is o-tolyl and R' is p-iodo-o-tolyl, R is o-tolyl and R' is m-nitro-phenyl, R is o-tolyl and R' is p-iodo-phenyl, R is phenyl and R' is p-bromo-o-tolyl, R is phenyl and R' is p-iodo-o-tolyl, R is phenyl and R' is m-nitro-phenyl, R is phenyl and R' is p-iodo-phenyl.

Contemplated equivalents of the foregoing compounds wherein one or both of R and R' are carbocyclic aryl are those wherein the aryl group is heterocyclic, e.g., 2- and 4-pyridyl, 2- and 3-N-methyl-pyrrolyl, 2- and 3- furamyl, 2- and 3-thiofuramyl, 2- and 3-benzofuramyl, 2-benzoxazolyl, etc.

Examples of those which have been isolated and/or prepared and found to possess the aforesaid in vitro ³H-DTG displacement activity are 1,3-dibutyl-guanidine, 1,3-diphenyl-guanidine, 1,3-(2'-methyl-4'-bromo-phenyl)-guanidine and 1,3-(2'-methyl-4'-iodo-phenyl-guanidine.

The level of sigma receptor activity of the disubstituted guanidines can also be determined in vivo in a discriminative stimulus property test employing rats trained to discriminate between intrapentoneal injections of cyclazocine (2. mg/kg) and saline in a discrete-trial avoidance paradigm with sessions of 20 trials each. For example, DTG and DPG were fully substitutable for cyclazocine at the same concentrations. (Holtzman, S. G., Emory University, Atlanta, Ga., private communication).

Although the discussion hereinafter of the experiments conducted by us relates to one of these selective sigma ligands, viz., 1,3-di-o-tolyl-guanidine (DTG), the activity and utility of that compound apply comparably to the other disubstituted guanidines which compete with and displace in vitro [³H]-1,3-di-o-tolyl- guanidine bound in vitro to isolated guinea pig brain membrane.

In carrying out the sigma receptor binding activity measurement method of this invention, a known amount of a mammalian brain membrane, e.g., human or other primate porcine, rodent, e.g., rat or guinea pig, which has SKF10,047 and like psychomimetic benzomorphan binding activity is contacted in a suitable aqueous vehicle, e.g., physiological saline solution, with a mixture, usually in a solution in a suitable aqueous vehicle of (i) a tritium labeled 1,3-disubstituted guanidine of this invention having sigma receptor binding activity, in an amount capable of being fully bound to the abovesaid amount of membrane and (ii) a water soluble organic compound whose sigma receptor activity is to be assayed, in known amounts, sufficiently varied to obtain a dose-response curve. The techniques for obtaining a dose-response curve are standard and well known to those skilled in the art. Typically, one could employ molar amounts varying as much as from $10^{-3}$ to $10^3$ of the molar amount of the tritium labeled compound present in the mixture, e.g., employing from 10 to 120 and preferably from 30 to 90 such mixtures.

If the organic compound being assayed has sigma receptor binding activity, a portion of the tritium labeled compound which, in the absence of the organic compound would bind to the membrane remains unbound and is thus separable from the membrane. The amount which remains unbound is proportional to the sigma receptor binding activity of the organic compound and the molar ratio thereof in the mixture to the tritium labeled compound.

The two compounds can be employed at any convenient collective concentration, e.g., from $10^{-8}$ to $10^3$ mM.

In the next step, the membrane is separated from and washed until free of the solution in which step (a) is conducted. In the next step, the amount of tritium labeled compound which is thus separated from the membrane is determined, e.g., by measuring the collective radioactivity-level of the separated solution and wash water and comparing that radioactivity to that obtained when the foregoing steps are conducted with the same amount of tritium labeled 1,3-disubstituted guanidine in the absence of the organic compound.

In the next step of the method, the activity of sigma receptor binding activity of the organic compound is determined from the dose response curve thus obtained.

All of the foregoing steps are conventional and have been employed in the prior art with other types of 3H-labeled compounds having sigma receptor binding activity. The method of this invention is, however, unique in that the tritium labeled 1,3-disubstituted guanidines of this invention are highly selective to binding by the sigma receptors and therefore will not compete with organic compounds which bind to other brain receptors.

These disubstituted guanidines can readily be prepared by conventional chemical reactions, e.g., when R and R' are the same, by reaction of the corresponding amine with cyanogen bromide. Other methods which can be employed includes the reaction of an amine with a preformed alkyl or allyl cyanamide. See Safer, S. R. et al., *J. Org. Chem.*, 13:924 (1948). This is the method of choice in our laboratory for producing 1,3-disubstituted guanidines in which the substituents are not identical. For a recent synthesis of unsymmetrical guanidines, see G. J. Durant et al., *J. Med. Chem.*, 28:1414 (1985).

The characterization of sigma receptors in vitro has been difficult because of the lack of selective drug ligands. Most benzomorphan opiates crossreact with other (mu, delta, kappa), opioid receptors and are therefore of only limited value for characterizing and isolating receptors. Pasternak et al.; (1981) *J. Pharmacol. Exp. Ther.* 219, 192–198; Zukin, R. S. & Zukin, S. R., (1981) *Mol. Pharm.* 20, 246–254; and Tam, S. W., (1985) *Eur. J. Pharmacol.* 109, 33–41. [$^3$H]DTG, binds specifically and with high affinity to a single class of binding sites in guinea pig brain membranes. The binding characteristics and the drug specificity profile of these sites are concordant with those proposed for the sigma receptor, including (1) naloxone insensitivity and stereoselectivity for dextrorotatory isomers of benzomorphan opiates such as (+)SKF 10,047, (+)cyclazocine and (+) pentazocine; (2) high affinity for haloperidol and certain phenothiazine anti-psychotic drugs; (3) stereoselectivity for (−)butaclamol; and (4) insensitivity to dopamine and apomorphine. [$^3$H]DTG is one of only two known compounds that are selective for the sigma site. The other, (+)[$^3$H]3-PPP, originally proposed to be a dopamine autoreceptor agonist, has recently been shown to be selective for sigma sites in rat brain membrane binding assays. Largent et al., (1984), supra. Our experiments confirm these findings in the guinea pig and shown that [$^3$H]DTG and (+)[$^3$H]3-PPP have virtually identical receptor binding characteristics and drug selectivity profiles. Previous studies have shown that sigma sites can also be labeled with (±)[$^3$H]SKF 10,047, (±)[$^3$H]ethylketazocine and with (±)[$^3$H]SKF 10,047. However, these ligands are not selective for the sigma site and require the presence of appropriate drugs in the binding assays to mask crossreacting non-sigma binding sites.

[$^3$H]DTG has a number of advantages as a sigma ligand. It is highly selective for the sigma site (unlike [$^3$H]SKF 10,047 and (±)[$^3$H]Ethylketazocine), it has a high degree of specific binding (90–97% of total binding) and it has a relatively simple chemical structure that is not chiral (unlike (+) [$^3$H]3-PPP and the benzomorphan opiates). These characteristics make it a good starting compound for the synthesis of analogs for structure-activity studies and for the design of irreversible sigma receptor ligands.

The sigma site labeled with [$^3$H]DTG is clearly not related to conventional (mu, delta, kappa) opioid receptors as it is naloxone insensitive and shows stereoselectivity for detrorotatory isomers of benzomorphan drugs. This is a reversed stereoselectivity compared to naloxonesensitive opioid receptors which are selective for levorotatory isomers of opiates. Sigma receptors should therefore not be referred to as sigma "opioid" receptors. The drug selectivity of sigma sites for dextrorotatory isomers of psychotomimetic opiates does, however, correlate well with the pharmacological profile of dextrorotatory versus levorotatory opiates in animal tests designed to differentiate between conventional opioid receptor activity and sigma (behavioral) activity of benzmorphan drugs. Cowan, A. (1981) *Life Sci.* 28, 1559–1570; Brady, K. T. et al, (1982) *Science* 215, 178–180; and Khazan, N. et al (1984) *Neuropharmacol.* 23, 983–987.

Autoradiography studies using [$^3$H]DTG visualize the sigma site in slide-mounted rodent brain sections and confirm that sigma sites are different from mu, delta, and kappa opioid receptors as the distribution of [$^3$H]DTG binding is rather distinct from the distribution of mu, delta, kappa opioid receptors. The anatomical distribution of [$^3$H]DTG binding sites is, however, very similar if not identical to the distribution of (+)[$^3$H]3-PPP binding sites, further confirming that the two radioligands label identical binding sites. The high affinity of the [$^3$H]DTG binding site for haloperidol and for certain phenothiazine antipsychotics (TABLE I) which are also dopamine $D_2$ receptor antagonists raises the question as to the relation of sigma receptors to dopamine $D_2$ receptors. The results presented show that the [$^3$H]DTG site is clearly distinct from dopamine $D_2$ receptors, since the autoradiographic distribution of dopamine receptor is dissimilar, and since dopamine and apomorphine do not interact with the [$^3$H]DTG binding site.

Furthermore the sigma site labeled with [$^3$H]is stereoselective for (−)butaclamol which is a reversed stereoselectivity compared to the dopamine $D_2$ receptors which are stereoselective for (+)butaclamol.

The haloperidol-sensitive sigma site labeled with [$^3$H]DTG was found to have a moderate affinity for the potent hallucinogen PCP in competition experiments. This is in agreement with findings by others who used (+)[$^3$H]SKF 10,047, [$^3$H](±)SKF 10,047 or (+)-[$^3$H3$-PPP to label sigma sites. In PCP receptor binding assays, however, [$^3$H]-PCP labeled predominantly (but not exclusively) a haloperidol-insensitive PCP binding site, termed PCP/sigma opiate receptor by Zukin and colleagues, Zukin et al., (1981, 1986) supra, which is separate from the haloperidol-sensitive sigma site labeled with [³H]DTG or (+)[³H]3-PPP. In contrast, [³H]DTG appears to label exclusively the haloperidol sensitive sigma site, since all specific binding is displacable by haloperidol and the anatomical distribution of [³H]DTG binding is distinct from the distribution of PCP receptors. Furthermore, unlabeled DTG is virtually inactive in a [³H]-PCP binding assay (S. William Tam, E. I. DuPont De Nemours & Co., Wilmington, Del., personal communication). There is some controversy as to which of the two binding sites is responsible for causing the behavioral effects of PCP and psychotomimetic benzomorphan opiates and would therefore correspond to the sigma receptor postulated by Martin et al., (1976), supra. Zukin and his collaborators have argued that the behavorial effects of both PCP and psychotomimetic benzomorphan opiates are mediated by the haloperidol-insensitive PCP site, to which benzomorphan opiates bind with moderate affinity. Largent et al., (1986), supra, cited circumstantial evidence suggesting that it is equally likely that the behavioral effects of both PCP and psychotomimetic opiates are mediated through the haloperidol-sensitive sigma site. As [³H]DTG exclusively labels the haloperidol sensitive sigma site and does not interact significantly with the haloperidol-insensitive PCP site, behavioral studies using DTG or other symmetrically substituted guanidines of this invention as prototypical sigma ligands should resolve this issue.

Perhaps the most important aspect of the findings on the drug specificity of sigma sites that have emerged from this and other studies is that they interact with certain very potent hallucinogenic drugs (haloperidol, phenothiazines) that are used clinically to treat schizophrenia. This intriguing drug selectivity profile facilitates studies aimed at investigating the role of sigma receptors in antipsychotic drug action and abnormal brain function. The availability of DTG and like N,N'-disubstituted guanidines as a selective sigma ligand should serve to facilitate such studies.

Like guanidines generally and 1,3-diphenyl-guanidine specifically, the disubstituted guanidines of this invention, including those of formula I, are accelerators for the vulcanization of rubbers, e.g., natural rubbers and epoxy group-containing acrylic rubber, and can be used for such purpose in the same manner as 1,3-diphenyl-guanidine. Thus [H³]-DTG can be incorporated into a vulcanized rubber object, e.g., a tire tread, and rate of loss of rubber therefrom by water can be monitored by rate of loss of radioactivity.

The compounds of this invention have highly selective affinity for sigma brains receptor. Consequently, they may have some of the activities of the benzomorphans, i.e., those produced by binding to the haloperidol-sensitive sigma receptor but not those produced by the binding of benzomorphans to other non-sigma receptors. For instance, benzomorphans may act at sigma receptors to cause mydriasis and tachycardia and their pronounced psychotomimetic effects. DTG is therefore an effective tool to demonstrate the physiological effects mediated by the sigma receptor which, to date, have been obscurred by cross-reactivity of benzomorphans with non-sigma receptors.

DTG may act in an agonistic, antagonistic or inverse agonistic manner in relation to the prototypical sigma benzomorphans. DTG can therefore be expected to affect pupil size, heart rate and mentation in a direction parallel or opposite that caused by benzomorphans which can be determined by standard tests in laboratory animals. The type and level of activity for a given dosage of each compound can be conventionally determined by routine experimentation using well known pharmacological protocols for each of the activities; the corresponding indications treatable at that dosage will be well known to skilled workers based on the pharmacological results. The compounds of this invention are particularly noteworthy for their antipsychotic activity to treat psychotic conditions by analogy to the known agents prolixin and Thorazine and for diagnosing sigma receptor intoxicated conditions.

The ³H-DTG of this invention is useful as a screening tool for compounds, such as the disubstituted guanidines of this invention, which are selective ligands for the sigma receptor binding site. As such, they are useful for the diagnosis and treatment of sigma receptor mediated hallucinogenic mental disorders. For example, such a compound which is an agonist to a putative natural ligand will temporarily exacerbate such a mental disorder which is the result of an overabundance of the endogenous ligand and will ameliorate a mental disorder which is the result of an abnormal insufficiency of the natural ligand. The converse occurs when the disubstituted guanidine is an antagonist to the putative endogenous ligand. In either case, the temporary alteration of the mental disorder by the administered ligand confirms that it is a sigma receptor associated disease, thereby eliminating other possible causes thereof, e.g., chemical toxicity, and facilitating the treatment thereof.

[³H]-DTG also binds to human brain membrane receptors with high affinity as determined in our laboratory. Therefore another use of [³H]-DTG is to explore the neurochemistry of mental disease by measuring the fluctations in receptor density or function in post-mortem tissue of patients manifesting psycho- or neuropathology as contrasted with tissue from normals (unaffected controls). This topic can be studied by both receptor binding assays and autoradiography.

The compounds of this invention can be administered orally or by injection, e.g., intramuscular, intraperitoneal or intravenously. The optimal dose can be determined by conventional means. Because most if not all of the disubstituted guanidines employed in this invention are substantially water insoluble, they are ordinarily administered in their protonated form, e.g., as a pharmaceutically acceptable salt of an organic or inorganic acid, e.g., hydrochloride, sulfate, hemi-sulfate, phosphate, nitrate, acetate, oxalate, citrate, etc.

The compounds of this invention can be employed in mixture with conventional excipients, i.e., pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising about 0.1 to about $10^3$ of the 1,3-disubstituted guanidine per each unit dosage.

Parenteral administration, e.g., i.p. or i.m., is preferred, the compounds of this invention being particularly valuable in the treatment of humans afflicted with a psychotic disease. In this regard, they can be employed in substantially the same manner as the known major tranquilizers.

It will be appreciated that the actual preferred amounts of active compounds used will vary according to the specific compound being utilized, the particular compositions formulated, the mode of application, and the particular site of administration. Optimal administration rates for a given protocol of administration can be readily ascertained by those skilled in the art using conventional dosage determination tests conducted with regard to the foregoing guidelines.

The sigma receptor binding activity of 1,3-di-o-tolyl-guanidine (DTG) was discovered during studies on the purification and characterization of an endogenous sigma receptor ligand. In the initial phases of this work numerous extraction solvents were tested for their suitability to extract endogenous sigma receptor ligand from cow brains. Certain extraction solvents (particularly acetone) contained an unidentified material that potently displaced (+)-[$^3$H]SKF 10,047 from guinea pig brain membrane binding sites. A receptor binding characterization of the material revealed that the binding activity was competitive, reversible and rather potent. Because of the potent sigma receptor binding properties of three compounds that were found in these solvents, these chemicals were purified to homogeneity using various reverse phase HPLC procedures and their structure determined. Their structure was determined by a combination of different methods including high resolution mass spectroscopy, nuclear magnetic resonance and UV-spectrophotometry. One of the three sigma receptor active chemicals that were purified from the extraction solvents proved to be 1,3-di-o-tolyl-guanidine (DTG).

After its structural characterization, synthetic DTG was tested in the (+)-[$^3$H]SKF 10,047 binding assay and was found to displace (+)-[$^3$H]SKF 10,047 from its brain membrane binding sites with a $K_i$ of 70 nM. The displacement was competitive and fully reversible.

The other two compounds that were isolated and characterized were di-phenyl-guanidine (DPG) and di-butyl-guanidine (DGB), both of which were active in the (+)-[$^3$H]SKF 10,047 binding assay.

Because of the high potency of DTG and related di-substituted guanidines to displace (+) [$^3$H]SKF 10,047 from its binding sites it was decided to synthesize a tritium labeled derivative of DTG. To do so, 1,3-di-(2-methyl-4-bromo-phenyl)-guanidine was subjected to catalytic reduction with tritium gas, which replaced the two bromine atoms with tritium atoms to produce 1,3-di-(p-[$^3$H]-o-tolyl)-guanidine, as described below.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

1,3-Di-(4-bromo-2-methylphenyl)-guanidine (4-Br-DTG)

To a stirred solution of cyanogen bromide (846 mg, 8.06 mmol) in distilled water (70 ml) was added in small portions 2.997 g (16.11 mmol) of 4-bromo-2-methylaniline (Aldrich, recrystallized from ether-pentane). A white precipitate formed during the addition. The mixture was stirred at 80° C. for 4 h. Upon cooling at 0° C. for 12 h, a sticky yellow oil separated out and was discarded. The clear aqueous phase was concentrated to about 30 ml. The white precipitate which formed was redissolved by heating the mixture. This was then set aside at 4° C. for 12 h. Filtration gave 430 mg of white solid. A 200-mg portion was dissolved in 10 ml of hot water and treated with 5 ml of 10% KOH solution. The mixture was extracted with CHCl$_3$ and the extract was washed with brine and then dried (MgSO$_4$). Evaporation of the solvent gave 171 mg of a brown solid which was crystallized from CHCl$_3$, giving 120 mg (8%) 4-Br-DTG as small white needles: mp 209°–210° C.; NMR (300 MH$_z$, CD$_3$OD, TMS) delta 2,24 (s, 3), 7.12–7.25 (AB, 2, J=8 Hz), 7.35 (s,l); IR (KBr) 3460, 3340, 1630 cm$^{-1}$. Analysis calculated for C$_{15}$H$_{15}$N$_3$—Br$_2$: C, 45.37; H, 3.81; N, 10.58. Found: C, 45.34; H, 3.56; N, 10.50.

[$^3$H]-1,3-di-ortho-tolyl-guanidine ([$^3$H]DTG)

Twenty-five mg (0.1 mmol) of the thus-produced 4-Br-DTG were submitted to Amersham Corporation (Arlington Heights, Ill.) for catalytic reduction in the presence of 20 Ci of [$^3$H]-gas. Two mCi portions of the crude, radioactive product in 0.2 m/each of 25% ethanol were purified by reverse phase high performance liquid chromatography (RP-HPLC) on a Vydac TP218 octadecasilica column using a CH$_3$CN gradient (0–35% in 60 minutes) in 0.1% trifluoroacetic acid for elution. Flow rate was 1 ml/min. One minute fractions were collected. Aliquots of the fractions were diluted 100 fold and 10 ul aliquots of the diluted fractions corresponding to 0.1 ul of the original fractions were dissolved in 10 ml scintillation fluid and counted in a scintillation spectrometer. The HPLC equipment consisted of 2 Waters HPLC pumps, and automated electronic gradient controller and a Kratos variable wave length UV spectrophotometer. The radioactivity eluted as a major, symmetrical peak coinciding with a major, symmetrical UV (220 nm) absorbing peak at 41 minutes. This is the same elution time at which authentic, unlabeled DTG emerges from the column in this RP HPLC system. The specific activity of [$^3$H]DTG was found to be 52 Ci/mmol based on the amount of DTG under the major UV absorbing peak as determined by quantitative UV-spectrophotometry and the amount of radioactivity associated with this peak as determined by quantitative liquid scintillation spectrometry.

Characteristics of [³H]DTG binding to guinea pig brain membranes

Synthesis of [³H]DTG resulted in a pure homogenous product of high specific radioactivity (52 Ci/mmol). [³H]DTG bound specifically, saturably, reversibly, and with high affinity to guinea pig brain membrane. In a typical experiment with 0.9 nM [³H]DTG (30,000 cpm, 50% counting efficiency) the total binding was 2,700 cpm while the nonspecific binding in the presence of 10 uM DTG or 10 uM haloperidol was 50-150 cpm. Routinely, a specific binding to 90-97% of total binding was observed. At room temperature the binding of [³H]DTG reached equilibrium after 60-90 minutes and it was fully reversible after addition of 10 uM unlabeled DTG. Specific binding was linear with tissue concentration between 2-40 mg tissue (original wet brain weight per assay tube). Binding of radioactivity to the glass fiber filters in the absence of membranes was 10-20 cpm. Boiling of membranes at 100° C. for 10 minutes prior to assay almost completely (90%) abolished specific [³H]DTG binding as did treatment of the membranes with trypsin and pronase (0.01 mg/ml for 30 min at room temperature), indicating that protein components are important for the receptors' binding ability.

To determine the equilibrium saturation binding of [³H]DTG to guinea pig brain membranes, membranes prepared as described herein were incubated with [³H]DTG at various concentrations from 0.3 nM to 90 mM in 1 ml 50 nM Tris/HCl buffer, pH 7.4, for 120 minutes at room temperature. Values obtained were the mean of quadruplicate determinations.

A Scatchard analysis of the saturation data shows a linear Scatchard plot with an apparent $K_D$ of 28 nM and a maximum number of binding sites (Bmax) of 84 pmol/g brain tissue (original wet weight). Analysis of the binding data with the curve fitting program LIGAND, Munson, P. J. & Rodbard, D., *Anal. Biochem.* 107, 220-239 showed high compatibility with a one site binding model.

Radioligand Binding Assays

Frozen guinea pig brains (Pel-Freeze, Rogers, AK) were homogenized in 10 volumes (w/v) of 0.32 M sucrose using a Polytron homogenizer. The homogenate was spun at 900×g for 10 minutes at 4° C. The supernatant was collected, and spun at 22,000 ×g for 20 minutes at 4° C. The pellet was resuspended in 10 volumes of 50 mM Tris/HCl buffer, pH 7.4, incubated at 37° C. for 30 minutes and spun again at 22,000 ×g for 20 minutes at 4° C. The pellet was then resuspended in 10 volumes of 50 mM Tris/HCl buffer, pH 7.4 and 10 ml aliquots of this membrane suspension were stored frozen at −70° C. until used in the binding assay. No effects of prolonged storage (>3 months) of the membranes at −70° C. on sigma receptor number or affinity for [³H]DTG binding were observed.

For radioreceptor assays aliquots of the frozen membrane suspension were thawed and diluted tenfold with 50 mM Tris/HCl buffer, pH 7.4. To 12×75 mm polystyrene or glass test tubes were added 0.8 ml of membrane suspension, 0.1 ml [³H]DTG or (+)[³H]3-PPP for a final concentration of 0.9 nM, and 0.1 ml of unlabeled drugs or buffer. The protein concentration in the 1 ml final incubation volume was 800 ug, corresponding to 32 mg of brain tissue (original wet weight). Nonspecific binding was defined as that remaining in the presence of either 10 uM DTG or haloperidol for both the [³H]DTG and the (+)[³H]3-PPP binding. After incubation for 90 minutes at room temperature the membrane suspension was rapidly filtered under vacuum through Whatman GF/B glass fiber filters using a Brandel 48 well cell harvestor (Brandel, Gaithersburg MD). The filters were washed with 3×5 ml ice-cold 50 mM Tris buffer (pH 7.4 at room temperature). The filters were dissolved in 10 ml each of Cytoscint (Westchem Products, San Diego, CA) and radioactivity was measured by liquid scintillation spectrometry at a counting efficiency of 35-50%. Saturation data were evaluated by Scatchard analysis using both the EBDA McPherson, G. A., (1983) *Computer Programs Biomed.* 17, 107-114 and LIGAND Munson, P. J. & Rodbard, D., (1980) *Anal Biochem.* 107, 220-239, data analysis programs on an IBM Personal Computer-AT. IC50 values were determined by plotting displacement curves onto semilogaroithmic graph paper followed by interpolation.

Drug Specificity of [³H]DTG Binding

Displacement experiments were performed with drugs that are considered typical sigma ligands, as well as with drugs considered to be prototypical ligands for other neurotransmitter, neuromodulator, and drug receptors. These experiments showed that the [³H]DTG binding site was stereoselective for dextrorotatory benzomorphan opiates and for (−)butaclamol; does not significantly interact with drugs that have high affinities for acetylcholine, benzodiazepine, GABA, nor with mu, delta, or kappa opioid receptors; and has a high affinity for haloperidol and several drugs belonging to the phenothiazine class of antipsychotics (haloperidol had the highest displacement potency of all drugs tested); and has a moderate affinity for several other classes of psychoactive drugs, which included several tricyclic antidepressants, PCP, and the kappa-opioid receptor ligand U50, 488H.

TABLE I

| Drug | IC50 against [³H]DTG (nM) (±SEM) | IC50 against (+)[³H]3-PPP(nM) (±SEM) |
|---|---|---|
| Haloperidol | 5 ± 0.3 | 17 ± 1 |
| DTG | 28 ± 1 | 53 ± 9 |
| Perphenazine | 42 ± 10 | 21 ± 3 |
| (+)Pentazocine | 43 ± 2 | 8 ± 3 |
| (−)Pentazocine | 135 ± 3 | 81 ± 1 |
| (±)Pentazocine | 69 ± 1 | ND |
| (+)3-PPP | 76 ± 4 | 33 ± 12 |
| (−)3-PPP | 280 ± 21 | 235 ± 60 |
| (+)Cyclazocine | 365 ± 25 | 47 ± 12 |
| (−)Cyclazocine | 2,600 ± 210 | 1,000 ± 0 |
| Spiperone | 690 ± 21 | ND |
| (−)Butaclamol | 530 ± 49 | 183 ± 5 |
| (+)Butaclamol | 2,150 ± 250 | 2,100 ± 71 |
| (+)SKF 10,047 | 625 ± 88 | 93 ± 5 |
| (−)SKF 10,047 | 4,000 ± 566 | 2,850 ± 390 |
| PCP | 1,050 ± 106 | 1,000 ± 71 |
| U50,488H | 1,350 ± 106 | ND |
| Trifluoperazine | 345 ± 4 | ND |
| Triflupromazine | 605 ± 67 | ND |
| Chlorpromazine | 1,475 ± 265 | ND |
| Amitriptyline | 300 ± 7 | ND |
| Imipramine | 520 ± 14 | ND |
| Desipramine | 4,000 ± 212 | ND |
| Nortriptyline | 2,000 ± 640 | ND |
| Guanabenz | 4,600 ± 283 | ND |
| Clonidine | >10,000 | ND |

TABLE I-continued

| Drug | IC$_{50}$ against [$^3$H]DTG (nM) ($\pm$SEM) | IC$_{50}$ against (+)[$^3$H]3-PPP(nM) ($\pm$SEM) |
| --- | --- | --- |
| Cocaine | >10,000 | ND |

*IC$_{50}$ is the molar concentration of the drug needed to produce half-maximal displacement of [$^3$H]DTG from sigma receptors. This is a direct measure of the sigma receptor binding potency of the drug.

The above IC$_{50}$s represent the average from 2-4 separate experiments (in triplicate). The following compounds caused no significant displacement at a 10 uM concentration: scopolamine, 5-OH-tryptamine, diazepam, bicuculline, picrotoxin, hexamethonium, dopamine, apomorphine, GABA, gamma-guanidino butyric acid, morphine, DAGO, metorphamide, dynorphin A, [leu$^5$]enkephalin, beta-endorphin, naloxone, guanidino acetic acid, creatine, creatinine, 1,1-di-methyl-guanidine, methyl-guanidine, beta-guanidino propionic acid, cimetidine (ND; not determined).

Drug specificity of [$^3$H]DTG binding compared to (+) [$^3$H]3-PPP binding

Comparing the drug specificity of [$^3$H]-DTG binding with that of (+)[$^3$H]3-PPP in the guinea pig, it was found that (+)[$^3$H]3-PPP bound specifically, saturably (linear Scatchard plot), reversibly and with high affinity to guinea pig brain membranes (K$_D$=30 nM, Bmax=80 pmol/g fresh brain weight). The drug specificity profile of the (+)[$^3$H]3-PPP binding in the guinea pig (TABLE I) was found to be very similar to that reported in the rat. Largent et al., (1984) supra. Moreover, the drug specificity profiles of typical sigma receptor active drugs in the (+) [$^3$H]3-PPP and [$^3$H]-DTG binding assays were highly correlated (r=0.95;p$\leq$0.00001) which is consistent with the two compounds labeling the same sites.

Autoradiography Studies

Male Sprague Dawley rats (200-250 g) and NIH guinea pigs (300-350 g) were sacrificed, their brains rapidly removed and processed for receptor autoradiography according to the method of Herkenham and Pert, Herkenham, M. & Pert, C. B., (1982) *J. Neuroscience* 2, 1129-1149.

Fifteen um thick slide-mounted brain sections were incubated for 45 minutes in 50 mM Tris-HCl (pH 8.0, 22° C.) containing 1 mg/ml bovine serum albumin (BSA) and 2 nM [$^3$H]DTG. Adjacent sections were incubated with 10 uM haloperidol or 10 uM DTG to measure nonspecific binding. Incubations were terminated by 4×2 minute washes in 10 mM Tris-HCL (pH 7.4, 4° C.) with 1 mg/ml BSA, rapidly dried under a stream of cool air and placed in x-ray cassettes with $^3$H-sensitive film ($^3$H-Ultrofilm, LKB). Films were developed 6-8 weeks later (D-19, Kodak).

Autoradiographic visualization of [$^3$H]DTG binding

Receptor autoradiography studies on guinea pig and rat brain sections using [$^3$H]DTG showed a low density of specific binding diffusely distributed throughout the gray matter of the rat and ginea pig brain. Superimposed on this homogeneous binding pattern was a heterogeneous distribution of enriched binding in limbic and sensorimotor structures. The pattern of binding was more distinct in the guinea pig than rat. Similar observations for (+) [$^3$H]3-PPP autoradiography have been reported. Largent et al., (1986) supra. Thus, description of [$^3$H]DTG binding was drawn primarily from the guinea pig. In the forebrain, limbic structures moderately to densely labeled by [$^3$H]DTG were the diagonal band of Broca, septum, hypothalamus (especially the paraventricular nucleus), anterodorsal thalamic nucleus and zona incerta. Sensorimotor thalamic nuclei moderately to densely labeled included the thalamic taste relay and reticular nuclei. Other thalamic nuclei labeled were the paraventricular and habenular nuclei. Very dense binding was seen in the choroid plexus. In the cortex dense [$^3$H]DTG labeling occupied layer III/IV of retrosplenial piriform, and entorhinal cortices. The rest of the cortex contained a low level of homogeneous binding. The hippocampal formation exhibited discrete binding in the pyramidal granular cell layers. Sensorimotor areas of the midbrain were selectively labeled by [$^3$H]DTG. The oculomotor nucleus, and more caudally, the trochlear nucleus were very densely labeled, and the superior colliculus and red nucleus had moderate levels of binding. Other midbrain nuclei labeled were the dorsal raphe, interpeduncular nucleus, central gray, and the substantia nigra, pars compacta. The selective labeling of the pars compacta in the guinea pig contrasted with the low to moderate density of labeling present throughout the substantia nigra of the rat. In addition, very dense binding was found in the subcommissural organ. In the hindbrain the locus coeruleus was the most densely labeled nucleus. Sensorimotor nuclei enriched in [$^3$H]DTG binding sites were the trigeminal motor nucleus, nucleus of the facial nerve, nucleus of the solitary tract, dorsal motor nucleus of the vagus, and hypoglossal nucleus. Moderate to dense binding was also found throughout the gray matter of the cerebellum, and in the pontine reticular nuclei.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. 1,3-Di-(4-halo-2-methylphenyl)-guanidine.

2. 1,3-Di-(p-[$^3$H]-o-tolyl)-guanidine.

3. A pharmaceutical composition, in unit dosage form and adapted for systemic administration to a human being, which comprises, per unit dosage, an amount effective to alter the sigma brain receptor-modulated activity of a human being, of a water soluble 1,3-disubstituted quanidine which displaces in vitro 1,3-di(p-[$^3$H]-1,3-di-o-tolyl-guanidine bound to isolated mammalian brain membrane.

4. A composition according to claim 3 wherein the guanidine is a compound of the formula

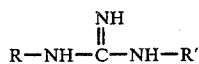

wherein R and R' each are an alkyl group of at least 4 carbon atoms cycloalkyl of 3-12 carbon atoms or carbocyclic or aryl groups of at least 6 carbon atoms.

5. A composition according to claim 4, wherein R and R' are the same group.

6. A composition according to claim 5, wherein R and R' are n-butyl.

7. A composition according to claim 5, wherein R and R' are o-tolyl.

8. A composition according to claim 5, wherein R and R' are phenyl.

9. A composition according to claim 5, wherein R and R' are 2-methyl-4-bromo-phenyl.

10. A composition according to claim 3, adapted for oral administration.

11. A composition according to claim 3, adapted for parenteral injection.

12. A composition according to claim 3, containing from about 0.1 mg to about 1 g of the disubstituted guanidines per unit dosage.

13. A method for determining the sigma brain receptor binding activity of an organic compound which comprises the steps of:
 (a) contacting in an aqueous medium a known amount of isolated mammalian brain membrane which has psychotomimetic benzomorphan binding activity, with a mixture of (i) a tritium labeled 1,3-disubstituted guanidine which selectively binds sigma brain receptors, in a known amount capable of being bound to the sigma receptors of that brain membrane; and (ii) varying known amounts of a water soluble organic compound to be assayed for sigma receptor binding activity;
 (b) separating the brain membrane from any of the tritium labeled compound which is not bound to the brain membrane in step (a);
 (c) determining, from the molar relationship of the proportion of bound tritium labeled compound which is separated in step (b) to the molar amount of the organic compound employed in step (a), the sigma receptor binding activity of that organic compound.

14. A method according to claim 13, wherein the tritium labeled compound is a disubstituted-guanidine of the formula

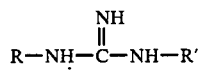

wherein R and R' each are an alkyl group of at least 4 carbon atoms cycloalkyl of 3–12 carbon atoms or carbocyclic or aryl groups of at least 6 carbon atoms.

15. A method according to claim 13, wherein the tritium labeled compound is 1,3-di(p-[$^3$H]-o-tolyl)-guanidine.

16. A method according to claim 13, wherein the brain membrane is porcine, rat, human or guinea pig.

17. A method according to claim 13, wherein the organic compound is a 1,3-disubstituted guanidine of the formula

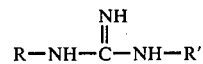

wherein R and R' each are an alkyl group of at least 4 carbon atoms cycloalkyl of 3–12 carbon atoms carbocyclic or aryl groups of at least 6 carbon atoms.

18. A method of determining the relationship of abnormal psychotic-like behavior in a mammal displaying such behavior to sigma receptor system dysfunction, which comprises administering the mammal displaying such behavior a water-soluble disubstituted-guanidine which displaces in vitro 1,3-di-(p-[$^3$H]-o-tolyl)-guanidine bound to mammalian brain membrane, an an amount effective to alter the sigma brain receptor-modulated mental activity of that mammal.

19. A method according to claim 18, wherein the mammal is a human being.

20. A method according to claim 19, wherein the human being is psychotic.

21. A method according to claim 18, wherein the substituted 1,3-di-o-tolyl-guanidine is a compound of the formula

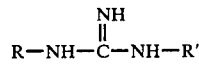

wherein R and R' are the same and each is a hydrocarbon group.

22. A method according to claim 21 wherein the mammal is a psychotic human being.

23. A method according to claim 22 wherein R and R' each are n-butyl, phenyl or -o-tolyl.

* * * * *

UNITED STATES PATENT AND TRADEMARK OFFICE
CERTIFICATE OF CORRECTION

PATENT NO. : 4,709,094

DATED : November 24, 1987

INVENTOR(S) : Weber, E. et al.

It is certified that error appears in the above-identified patent and that said Letters Patent is hereby corrected as shown below:

Column 1, immediately before "BACKGROUND OF THE INVENTION" please insert the following text:

--STATEMENT AS TO RIGHTS TO INVENTIONS MADE UNDER FEDERALLY SPONSORED RESEARCH AND DEVELOPMENT

This invention was made with government support under Grant No. MH 40303 awarded by the National Institutes of Health. The government has certain rights in the invention.--

Signed and Sealed this

Twenty-third Day of February, 1993

*Attest:*

STEPHEN G. KUNIN

*Attesting Officer*    *Acting Commissioner of Patents and Trademarks*